United States Patent
Samaritani et al.

(10) Patent No.: US 7,540,382 B2
(45) Date of Patent: Jun. 2, 2009

(54) STABILIZED LIQUID PROTEIN FORMULATIONS IN PHARMACEUTICAL CONTAINERS

(75) Inventors: Fabrizio Samaritani, Rome (IT); Alessandra Del Rio, Rome (IT)

(73) Assignee: Ares Trading S.A., Aubonne (CH)

( * ) Notice: Subject to any disclaimer, the term of this patent is extended or adjusted under 35 U.S.C. 154(b) by 118 days.

(21) Appl. No.: 10/556,467

(22) PCT Filed: May 12, 2004

(86) PCT No.: PCT/EP2004/050779

§ 371 (c)(1),
(2), (4) Date: Nov. 16, 2006

(87) PCT Pub. No.: WO2004/100979

PCT Pub. Date: Nov. 25, 2004

(65) Prior Publication Data

US 2007/0092487 A1    Apr. 26, 2007

(30) Foreign Application Priority Data

May 13, 2003 (EP) .................................. 03010671

(51) Int. Cl.
*B65D 1/09* (2006.01)
*B65D 83/04* (2006.01)
*B65D 85/42* (2006.01)
*A61K 38/21* (2006.01)
*C08F 14/18* (2006.01)
*C08F 114/18* (2006.01)
*C08F 214/18* (2006.01)

(52) U.S. Cl. .................. 206/528; 424/85.6; 526/255
(58) Field of Classification Search .................. None
See application file for complete search history.

(56) References Cited

U.S. PATENT DOCUMENTS

| | | | | |
|---|---|---|---|---|
| 5,183,746 A | * | 2/1993 | Shaked et al. | 435/69.51 |
| 5,661,125 A | | 8/1997 | Strickland | |
| 6,171,586 B1 | * | 1/2001 | Lam et al. | 424/130.1 |
| 2004/0043973 A1 | * | 3/2004 | Ahlem et al. | 514/179 |

FOREIGN PATENT DOCUMENTS

| | | |
|---|---|---|
| EP | 0 641 567 | 3/1995 |
| EP | 0 736 303 | 10/1996 |
| WO | 97/17087 | 5/1997 |
| WO | 98/28007 | 7/1998 |

* cited by examiner

*Primary Examiner*—Robert Landsman
(74) *Attorney, Agent, or Firm*—Oblon, Spivak, McClelland, Maier & Neustadt, P.C.

(57) ABSTRACT

A container comprising a closure means coated by an inert fluorinated material and containing a liquid pharmaceutical composition. In particular, the container comprises a closure means coated by TEFLON (polytetrafluoruethylene (PTFE)) and contains a HSA-free Interferon-β formulation having the following composition: 30 to 100 μg/ml of interferon-β, an isotonicity agent, 0.1 to 2 mg/ml of Poloxamer 188, at least 0.12 mg/ml of L-Methionine and a buffer solution capable of maintaining the pH of the liquid formulation at a value between 3.0 and 4.0.

12 Claims, No Drawings

STABILIZED LIQUID PROTEIN FORMULATIONS IN PHARMACEUTICAL CONTAINERS

TECHNICAL FIELD

The present invention relates to a container containing a liquid pharmaceutical composition for injectables and containing a protein as active ingredient.

BACKGROUND ART

Medicines for injection are not always available from the manufacturer in a ready-to-use form. Therefore, many injections need to be prepared before they can be administered.

The process of preparation may be straightforward, for example a simple dilution, or complicated, for example involving complex calculations, or several manipulations. There are the risks of error in the calculations and during the manipulations involved, and risks of microbial and particulate contamination. The nature of the medicine and the clinical condition of the patient may affect the degree of the overall risk.

The risk of contamination is higher when injections are prepared in environments without suitable controls. Over the past thirty years, surveys on intravenous medicines prepared in near-patient areas have shown a range of contamination rates ranging from 2 to 15% (average 8%). Although most of the contamination does not lead to sepsis, the nature of the contaminating organism cannot be predicted. Therefore the risk of serious sepsis cannot be discounted, particularly if the patient is immunocompromised, or if the injection solution supports bacterial growth.

Therefore there is an increasing need for liquid pharmaceutical compositions in a ready-to-use form, i.e. ready for injection. These kinds of pharmaceutical compositions are normally sold in suitable sterile containers like vials, pre-filled syringes, ampoules, small bottle, tubues or cartridges for autoinjectors.

The preparation of liquid protein formulations for pharmaceutical compositions in a ready-to-use form is generally interfered by the low stability of the protein. In fact, it is known that proteins in the purified form are highly susceptible to degradation, even due to the normal activity of atmospheric agents. This particularity becomes even more evident for proteins produced according to recombinant DNA techniques.

The stability problem is particularly felt for interferon-β formulations, which do not comprise human serum albumin (HSA) as stabilizing agent. Nowadays formulations without HSA are preferred because HSA has two main drawbacks: the first is related to its extraction from human blood and, hence, the possibility of infection transmission, the second refers to its high cost due to its low availability.

Moreover the liquid pharmaceutical compositions may be for single-dose use or for multiple-dose use. In particular, when multi-dose are prepared, it may become necessary to add some additional excipients, which are the preservatives or bacteriotastic agents, to prevent microbial contamination after the container is opened or perforated by a needle due to repeated administrations from the same container.

Although the use of such bacteriostatic agents is necessary for the reason above, it has a negative effect on proteins stability. Because of this, the amount of bacteriostatic agents used in the multidose protein formulation has to be very low. In this case, besides the absence of contamination is not highly guaranteed, the proteins are not stable for the intended use.

To well understand the protein stability problem in the formulations for a multidose product, it has to be underlined the importance that multidose products have in the current pharmaceutical market. In fact, in the most of therapies the liquid pharmaceutical protein formulations have to be injected very often. For instance, liquid interferon-beta formulations for the treatment of multiple sclerosis have to be administered every given day to once a week depending on both the kind of interferon-beta used and if the injection is intramuscular or subcutaneous.

Because of such a frequent use of the formulations, in the last years the liquid pharmaceutical protein formulations are prepared as multidose formulations in containers that the patient can use also by using an injector device. As it is easy to understand, multidose formulations will ease the patient life.

Therefore, the need was felt to find specific conditions for obtaining liquid protein pharmaceutical composition ready for injection, having an improved stability, and being usable for both monodose and multidose use.

DISCLOSURE OF INVENTION

The Applicant has surprisingly and unexpectedly found particular containers useful to solve the above technical problem.

The main object of the present invention is the use of a closure means coated by an inert fluorinated material for a container of a liquid pharmaceutical composition ready for injection and containing a protein as active ingredient.

More preferably, the protein is an Interferon.

Preferably, the Interferon is an Interferon-β.

Another object of the present invention is a container containing a liquid pharmaceutical composition ready for injection and containing a protein as active ingredient, characterised by comprising a closure means coated by an inert fluorinated material.

More preferably, the inert fluorinated material is TEFLON®.

The container may be a vial, a pre-filled syringe, an ampoule, a small bottle, a tube or a cartridge for autoinjector, or any other suitable container for injectable formulations.

In the case of a syringe or a cartridge, the closure means is a plunger, whereas in the case of vials, tubes, ampoules or bottles the closure means is a stopper. The closure means may be made of rubber or another synthetic or natural polymeric material suitable for that purpose.

Preferably the container is made of glass. More preferably, the internal surface of the container is coated by an inert material. Most preferably, this inert material coating the internal glass surface of the container is silicon.

Preferably, the liquid pharmaceutical composition contains a bacteriostatic agent.

Preferably, the bacteriostatic agent is present at a concentration comprised between about 2 and 9 mg/ml.

Preferably, the bacteriostatic agent is benzyl alcohol.

Preferably, the liquid pharmaceutical composition is a liquid HSA-free formulation comprising 30 to 100 μg/ml of interferon-β, an isotonicity agent, 0.1 to 2 mg/ml of a surfactant, at least 0.12 mg/ml of an antioxidant and a buffer solution capable of maintaining the pH of the liquid formulation at a value between 3.0 and 4.0.

The term "buffer" or "physiologically-acceptable buffer" refers to solutions of compounds that are known to be safe for pharmaceutical or veterinary use in formulations and that have the effect of maintaining or controlling the pH of the formulation in the pH range desired for the formulation. Acceptable buffers for controlling pH at a moderately acidic pH to a moderately basic pH include, but are not limited to, such compounds as phosphate, acetate, citrate, arginine, TRIS, and histidine. "TRIS" refers to 2-amino-2-hydroxymethyl-1,3,-propanediol, and to any pharmacologically acceptable salt thereof. Preferable buffers are acetate buffers with saline or an acceptable salt.

An "isotonicity agent" is a compound that is physiologically tolerated and imparts a suitable tonicity to a formulation to prevent the net flow of water across cell membranes that are in contact with the formulation. Compounds such as glycerin, are commonly used for such purposes at known concentrations. Other suitable isotonicity agents include, but are not limited to, amino acids or proteins (e.g., glycine or albumin), salts (e.g., sodium chloride), and sugars (e.g., dextrose, mannitol, sucrose and lactose). Preferably the isotonicity agent is mannitol.

The term "antioxidant" refers to a compound that prevents oxygen or oxygen-derived free radicals from interacting with other substances. Antioxidants are among a number of excipients commonly added to pharmaceutical systems to enhance physical and chemical stability. Antioxidants are added to minimize or retard oxidative processes that occur with some drugs or excipients upon exposure to oxygen or in the presence of free radicals. These processes can often be catalyzed by light, temperature, hydrogen on concentration, presence of trace metals or peroxides. Sulfites, bisufites, thiourea, methionine, salts of ethylenediaminetetraacetic acid (EDTA), butylated hydroxytoluene (BHT), and butylated hydroxy anisole (BHA) are frequently used as antioxidants in drugs. Sodium EDTA has been found to enhance the activity of antioxidants by chelating metallic ions that would otherwise catalyze the oxidation reaction. Most preferred antioxidant is methionine The term "bacteriostatic" refers to a compound or compositions added to a formulation to act as an anti-bacterial agent. A preserved formulation of the present invention preferably meets statutory or regulatory guidelines for preservative effectiveness to be a commercially viable multi-use product. Examples of bacteriostatics include phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal. Preferably the bacteriostatic agent is benzyl alcohol.

The term "surfactant" refers to a soluble compound that reduces the surface tension of liquids, or reduces interfacial tension between two liquids or a liquid and a solid, the surface tension being the force acting on the surface of a liquid, tending to minimize the area of the surface. Surfactants have sometimes been used in pharmaceutical formulations, including delivery of low molecular mass drugs and polypeptides, in order to modify the absorption of the drug or its delivery to the target tissues.

According to a preferred embodiment of the invention, it has been found that by formulating interferon with a surfactant selected from Pluronic® F77, Pluronic F87, Pluronic F88 and Pluronic® F68, particularly preferably Pluronic F68 (BASF, Pluronic F68 is also known as Poloxamer 188) they obtain stable formulations that minimise the loss of active principle caused by adsorption on the surfaces of the vial and/or delivery device (e.g. syringe, pump, catheter, etc.). It has also been found that by formulating interferon with a surfactant selected from Pluronic® F77, Pluronic F87, Pluronic F88 and Pluronic® F68, particularly preferably Pluronic F68 (BASF, Pluronic F68 is also known as Poloxamer 188) they obtain a stable formulation, which is more resistant to oxidation and to formation of proteins aggregates.

"HSA" stands for Human Serum Albumin.

An "active ingredient" is intended to mean a substance that furnish pharmacological activity or other direct effect in the diagnosis, cure, mitigation, treatment, or prevention of disease or to affect the structure or any function of the body.

"Excipient" is intended to mean anything other than the active ingredient in a pharmaceutical composition.

BEST MODE FOR CARRYING OUT THE INVENTION

The present invention will now be described by way of a number of non-limiting, purely illustrative examples.

EXAMPLES

In the examples below the compatibility of monodose and multidose formulations of interferon-β-1a with primary packaging material is evaluated in different cartridges and different rubber closure means. In particular, for a good evaluation of the invention, every formulation has been stored under the same conditions except for the closure means.

The different formulations are tested for oxidised forms of proteins(RP-HPLC method) and aggregates (SE-HPLC method) upon storage at 40° C. and 25° C.

Example 1

Monodose HSA-Free Interferon-β-1a Formulation

A formulation (A) having the following composition has been prepared:
Formulation
88 mcg/ml IFN-β-1a in sodium acetate buffer pH 3.5
54.6 mg/ml mannitol,
1 mg/ml Poloxamer 188
0.12 mg/ml L-Methionine.

The manufacturing process consists in mixing the drug substance directly with the ingredients; then an aseptic filtration is performed followed by filling of the containers.

A description of each step of the process is given hereafter:
 an appropriate quantity of glacial acetic acid is added to WFI and the pH is adjusted to 3.5±0.2 using 1 M NaOH or 50% diluted acetic acid. The solution is completed to final volume using WFI;
 a calculated amount of excipients (mannitol, Poloxamer 188, L-Methionine) to respect the composition of formulation is weighed and dissolved in the required amount of 0.01 M sodium acetate buffer pH 3.5; the pH is then checked and adjusted, if needed, to 3.5±0.2 with 1 M NaOH or 50% diluted acetic acid; the solution is then completed to final weight with 0.01 M sodium acetate buffer;
 a calculated amount of IFN-β-1a drug substance is added to the required amount of excipient solution and gently stirred to homogeneity;
 the solution is then filtered through a 0.2 μm nylon membrane (Ultipor $N_{66}$ 0.2 μm, Pall), mounted into a stainless steel holder, under nitrogen pressure (1 bar max) and collected into a sterile container.

Once prepared, the formulation A has been packaged using different cartridges and closure means as described in Table I

TABLE I

| FORMULATION | CARTRIDGE | CLOSURE MEANS |
|---|---|---|
| A1 | Non-siliconized | Coated plunger |
| A1 comp. | Non-siliconized | Non-coated plunger (1) |
| A2 | Siliconized | Coated plunger |
| A2 comp. | Siliconized | Non-coated plunger (1) |

Materials used:

Non-siliconized cartridge (3 mL type I borosilicate glass cartridges, Nuova OMPI)

Siliconized cartridge (3 mL type I borosilicate glass cartridges, Nuova OMPI)

Coated plunger (Omniflex FM257/2, Helvoet Pharma—coating material is TEFLON "(polytetrafluoruethylene (PTFE))".

Non-coated plunger (1) (FM 257/5 Helvoet Pharma)

Example 1a

Experimental Tests

The A formulations packaged as described in TABLE I have been stored at 25±2° C. and 40±2° C., and tested for stability In Table II the results of the analytical test of A formulations stored at 40° C. are summarized.

TABLE II

| FORMULATION | T = 0 | T = 2 WEEKS | T = 3 WEEKS |
|---|---|---|---|
| | % Oxidised forms | | |
| A1 | 1.7 | 2.8 | 3.9 |
| A1 comp. | 2.1 | 4.6 | 13.2 |
| A2 | 0.9 | 2.4 | 2.2 |
| A2 comp. | 0.8 | 4.4 | 9.2 |
| | % Total aggregates | | |
| A1 | 3.4 | 3.1 | 3.0 |
| A1 comp. | 3.4 | 2.8 | 2.7 |
| A2 | 1.7 | 2.0 | 1.5 |
| A2 comp. | 1.8 | 2.8 | 2.1 |

In Table III the results of the analytical test of A formulations stored at 25° C. are summarized.

TABLE III

| FORMULATION | T = 0 | T = 4 WEEKS | T = 8 WEEKS | T = 12 WEEKS |
|---|---|---|---|---|
| | % Oxidised forms | | | |
| A1 | 1.7 | 2.4 | 2.1 | 2.1 |
| A1 comp. | 2.1 | 3.5 | 4.8 | 4.9 |
| A2 | 0.9 | 1.0 | | |
| A2 comp. | 0.8 | 1.6 | | |
| | % Total aggregates | | | |
| A1 | 3.4 | 2.8 | 3.8 | 3.2 |
| A1 comp. | 3.4 | 1.6 | 1.8 | 1.4 |
| A2 | 1.7 | 1.4 | | |
| A2 comp. | 1.8 | 1.6 | | |

Out of TABLE II and TABLE III it can be seen that formulations A have a good stability (see oxidised percentage) only when stored in a container with closure means coated by TEFLON "(polytetrafluoruethylene (PTFE))", regardless the cartridge material. The stability difference is even more evident when the formulation A is stored at 40° C. (TABLE II).

Different packaging conditions do not seem to affect the aggregates percentage.

Example 2

Multidose HSA-Free Interferon-β-1a Formulation

Three formulations (B-D) having the compositions (mg/mL) illustrated in TABLE IV have been prepared.

TABLE IV

| FORMULATION | IFN-β-1a | Mannitol | Poloxamer 188 | L-Met | Benzyl Alcohol | Acetate 10 mM pH 3.5 |
|---|---|---|---|---|---|---|
| B | 0.088 | 54.6 | 1 | 0.12 | 5 | Qs 1 mL |
| C | 0.088 | 54.6 | 1 | 0.12 | 7 | Qs 1 mL |
| D | 0.088 | 54.6 | 1 | 0.12 | 9 | Qs 1 mL |

In this case, the presence of benzyl alcohol as bacteriostatic agent allows the use of these formulations in pharmaceutical products for a multidose administration.

The formulations B-D have been prepared in the same way described in example 1 for formulation A, except for the inclusion of benzyl alcohol in the excipients solution.

After the preparation, the formulations B-D have been packaged using different cartridges and closure means as described in Table V

TABLE V

| FORMULATION | CARTRIDGE | CLOSURE MEANS |
|---|---|---|
| B1 | Non-siliconized | Coated plunger |
| B1 comp. | Non-siliconized | Non-coated plunger (1) |
| B2 | Siliconized | Coated plunger |
| B2 comp | Siliconized | Non-coated plunger (1) |
| C | Siliconized | Coated plunger |
| C comp. | Siliconized | Non-coated plunger (2) |
| D | Siliconized | Coated plunger |
| D comp. | Siliconized | Non-coated plunger (2) |

In this case, in addition to the materials described in example 1, a new closure means has been used:

Non-coated plunger (2) (4023/50, West Pharmaceutical)

Example 2a

Experimental Tests

Formulations B-D packaged as described in TABLE V have been stored at 25±2° C. and 40±2° C., and tested for stability In Table VI the results of the analytical test of B-D formulations stored at 40° C. are summarized.

TABLE VI

| FORMULATION | T = 0 | T = 2 WEEKS | T = 3 WEEKS |
|---|---|---|---|
| | % Oxidised forms | | |
| B1 | 1.7 | 3.1 | 4.1 |
| B1 comp. | 2.1 | 9.8 | 12.0 |
| B2 | 1.7 | 2.9 | 3.3 |
| B2 comp. | 1.5 | 6.5 | 14.2 |
| C | 1.2 | 3.0 | 3.3 |
| C comp. | 0.9 | 4.4 | 10.3 |

TABLE VI-continued

| FORMULATION | T = 0 | T = 2 WEEKS | T = 3 WEEKS |
|---|---|---|---|
| D | 1.1 | 3.5 | 3.5 |
| D comp. | 1.0 | 5.5 | 14.1 |
| % Total aggregates | | | |
| B1 | 3.4 | 3.5 | 3.4 |
| B1 comp. | 3.2 | 6.4 | 14.9 |
| B2 | 1.6 | 2.6 | 2.4 |
| B2 comp. | 1.6 | 10.5 | 11.4 |
| C | 1.7 | 3.2 | 2.6 |
| C comp. | 1.6 | 16.9 | 21.1 |
| D | 1.9 | 4.6 | 4.2 |
| D comp. | 1.7 | 31.7 | 56.5 |

In Table VII the results of the analytical test of B-D formulations stored at 25° C. are summarized.

TABLE VII

| FORMULATION | T = 0 | T = 4 WEEKS | T = 8 WEEKS | T = 12 WEEKS |
|---|---|---|---|---|
| % Oxidised forms | | | | |
| B1 | 1.7 | 2.3 | 2.7 | 2.7 |
| B1 comp. | 2.1 | 3.6 | 4.7 | Not measurable |
| B2 | 1.7 | 1.7 | | |
| B2 comp. | 1.5 | 2.4 | | |
| C | 1.2 | 1.4 | | |
| C comp. | 0.9 | 1.5 | | |
| D | 1.1 | 2.0 | | |
| D comp. | 1.0 | 2.0 | | |
| % Total aggregates | | | | |
| B1 | 3.4 | 2.8 | 3.7 | 3.1 |
| B1 comp. | 3.2 | 1.5 | 2.3 | 2.1 |
| B2 | 1.6 | 1.4 | | |
| B2 comp. | 1.6 | 1.4 | | |
| C | 1.7 | 1.6 | | |
| C comp. | 1.6 | 1.5 | | |
| D | 1.9 | 1.7 | | |
| D comp. | 1.7 | 1.9 | | |

From the results shown in TABLE VI and TABLE VII it can be noted a higher stability of the formulations stored with closure means coated by TEFLON "(polytetrafluoruethylene (PTFE))"regardless the cartridge material.

In particular, in this example it has been shown that also formulations comprising bacteriostatic agent can reach a very good stability when stored in containers with closure means coated by TEFLON "(polytetrafluoruethylene (PTFE))". This is true even if they contain a large amount of bacteriostatic agent. In fact, as it is shown (in particular in TABLE VI), for the formulations stored with non-coated closure means the presence of bacteriostatic agent is responsible for the very low protein stability.

Such a good stability for this kind of formulation is very important to obtain a pharmaceutical multidose product as it has been said above.

The invention claimed is:

1. A method for containing a composition comprising providing a liquid pharmaceutical composition ready for injection and comprising an interferon β as an active ingredient into a container which is a vial, an ampoule, a small bottle or a tube with a closure stopper wherein the closure stopper is coated with polytetrafluoruethylene (PTFE).

2. The method according to claim 1, wherein the liquid pharmaceutical composition contains a bacteriostatic agent.

3. The method according to claim 2, wherein the bacteriostatic agent is benzyl alcohol.

4. The method according to claim 2, wherein the bacteriostatic agent is present at a concentration between about 2 and 9 mg/ml.

5. A method for containing a composition comprising providing a liquid pharmaceutical composition ready for injection and comprising a protein as an active ingredient into a container with a closure article coated with polytetrafluoruethylene, wherein the pharmaceutical composition is a liquid HSA-free (human serum album) formulation comprising 30 to 100 µg/ml of interferon-β, an isotonicity agent, 0.1 to 2 mg/ml of a surfactant, at least 0.12 mg/ml of an antioxidant and a buffer solution capable of maintaining the pH of the liquid formulation at a value between 3.0 and 4.0.

6. A container for a liquid pharmaceutical composition containing an interferon β as active ingredient, wherein the container is a vial, an ampoule, a small bottle or a tube and a closure stopper which is coated with polytetrafluoruethylene (PTFE).

7. The container according to claim 6, wherein the container is made of glass.

8. The container according to claim 6, wherein the internal surface of the container is coated by an inert material.

9. The container according to claim 6, wherein the inert material coating the internal glass surface of the container is silicon.

10. The container according to claim 6, wherein the closure stopper is made of rubber.

11. The container according to claim 6, wherein the container is a pre-filled syringe or a cartridge for autoinjector and the closure stopper is a plunger.

12. A pharmaceutical product comprising a container according claim 6.

* * * * *